United States Patent

Oosterwijk et al.

(10) Patent No.: US 9,605,075 B2
(45) Date of Patent: *Mar. 28, 2017

(54) HYBRIDOMA CELL LINE G250 AND ITS USE FOR PRODUCING MONOCLONAL ANTIBODIES

(75) Inventors: Egbert Oosterwijk, Beuningen (NL); Sven Warnaar, Leiden (NL); Stefan Ullrich, Munich (DE)

(73) Assignee: WILEX AG, Munich (DE)

( * ) Notice: Subject to any disclaimer, the term of this patent is extended or adjusted under 35 U.S.C. 154(b) by 1146 days.

This patent is subject to a terminal disclaimer.

(21) Appl. No.: 12/342,512

(22) Filed: Dec. 23, 2008

(65) Prior Publication Data

US 2009/0274620 A1   Nov. 5, 2009

Related U.S. Application Data

(60) Division of application No. 11/655,110, filed on Jan. 19, 2007, which is a continuation of application No. 10/470,940, filed as application No. PCT/EP02/01282 on Feb. 7, 2002, now abandoned.

(60) Provisional application No. 60/266,853, filed on Feb. 7, 2001, provisional application No. 60/327,008, filed on Oct. 5, 2001.

(51) Int. Cl.
| C07K 16/00 | (2006.01) |
| C07K 16/30 | (2006.01) |
| A61K 47/48 | (2006.01) |
| A61K 39/00 | (2006.01) |

(52) U.S. Cl.
CPC .... *C07K 16/3038* (2013.01); *A61K 47/48607* (2013.01); *A61K 2039/505* (2013.01); *C07K 2317/24* (2013.01); *C07K 2317/56* (2013.01); *C07K 2317/565* (2013.01)

(58) Field of Classification Search
USPC ....................................................... 424/130.1
See application file for complete search history.

(56) References Cited

U.S. PATENT DOCUMENTS

| 4,816,567 | A | 3/1989 | Cabilly et al. |
| 5,104,652 | A | 4/1992 | Houghton et al. |
| 5,387,676 | A | 2/1995 | Zavada et al. |
| 5,530,101 | A | 6/1996 | Queen et al. |
| 5,618,920 | A | 4/1997 | Robinson et al. |
| 5,772,997 | A | 6/1998 | Hudziak et al. |
| 5,807,715 | A | 9/1998 | Morrison et al. |
| 5,830,452 | A | 11/1998 | Bauer et al. |
| 5,955,075 | A | 9/1999 | Zavada et al. |
| 5,972,353 | A | 10/1999 | Zavada et al. |
| 5,981,711 | A | 11/1999 | Zavada et al. |
| 5,989,838 | A | 11/1999 | Zavada et al. |
| 6,004,535 | A | 12/1999 | Zavada et al. |
| 6,027,887 | A | 2/2000 | Zavada et al. |
| 6,051,226 | A | 4/2000 | Zavada et al. |
| 6,069,242 | A | 5/2000 | Zavada et al. |
| 6,093,548 | A | 7/2000 | Zavada et al. |
| 6,204,370 | B1 | 3/2001 | Zavada et al. |
| 6,297,041 | B1 | 10/2001 | Zavada et al. |
| 6,297,051 | B1 | 10/2001 | Zavada et al. |
| 6,331,415 | B1 | 12/2001 | Cabilly et al. |
| 6,770,438 | B2 | 8/2004 | Zavada et al. |
| 6,774,117 | B1 | 8/2004 | Zavada et al. |
| 7,045,605 | B2 | 5/2006 | Bander et al. |
| 7,381,801 | B2 | 6/2008 | Renner et al. |
| 7,456,008 | B2 | 11/2008 | Lindholm et al. |
| 7,632,496 | B2 | 12/2009 | Warnaar et al. |
| 7,691,375 | B2 * | 4/2010 | Wilhelm et al. ........... 424/133.1 |
| 7,714,113 | B2 | 5/2010 | Renner et al. |
| 2003/0027994 | A1 | 2/2003 | Anderson et al. |
| 2004/0077081 | A1 | 4/2004 | Oosterwijk et al. |
| 2004/0132007 | A1 | 7/2004 | Lindholm et al. |
| 2004/0219633 | A1 | 11/2004 | Bolhuis et al. |
| 2008/0138275 | A1 | 6/2008 | Oosterwijk et al. |
| 2009/0162382 | A1 | 6/2009 | Bernett et al. |
| 2009/0252683 | A1 | 10/2009 | Kischel et al. |
| 2009/0274620 | A1 | 11/2009 | Oosterwijk et al. |
| 2010/0008888 | A1 | 1/2010 | Warnaar et al. |
| 2010/0167395 | A1 | 7/2010 | Renner et al. |
| 2011/0123537 | A1 | 5/2011 | Wohl et al. |

FOREIGN PATENT DOCUMENTS

| EP | 0210970 A2 | 2/1987 |
| EP | 1749839 A1 | 7/2007 |
| WO | 93/18152 A1 | 9/1993 |
| WO | WO 97/41831 A1 | 11/1997 |
| WO | 8808854 A1 | 11/1998 |
| WO | 9954342 A1 | 10/1999 |
| WO | 0067792 A1 | 11/2000 |
| WO | 01/02431 A1 | 1/2001 |

(Continued)

OTHER PUBLICATIONS

Riethmuller et al (Curr., Opin. Imm., 5:732-739, 1993).*
Bleumer et al (European Urology Supplements vol. 1 p. 112, abstract 437, Jan. 2002).*
Divgi et al (PASCO, 14:abstract 1345, 1995).*
Kranenberg et al (Cancer Research, 55:5864s-5867s, 1995).*
Oosterwijk et al ( Sem. Onc., 22(1):34-41, 1995).*
Weijtens, "Chimeric scFv/y receptor-mediated T-cell lysis . . . ", Int. J. Cancer 77 (1998), 181-187.
Uemura et al., "Internal image anti-idiotype antibodies related to renal-cell carcinoma-assoicated antigen G250", Int. J. Cancer 56 (1994), pp. 609-614.(Abstract).
Zavada et al., "Human tumour-associciated cell adhesion protein MN/CA IX: identification of M75 eptiope and of the region mediating cell adhesion", Br. J. Cancer 82 (2000), 1808-1813.

(Continued)

*Primary Examiner* — Brad Duffy
(74) *Attorney, Agent, or Firm* — Kilpatrick Townsend & Stockton LLP

(57) ABSTRACT

This invention relates to a hybridoma cell line which is capable of producing the monoclonal antibody G250. Furthermore, the invention describes the method of employing such cell line for the production and manufacture of monoclonal antibody G250 as well as derivatives thereof such as chimeric and humanized G250 antibodies.

24 Claims, 2 Drawing Sheets

(56) References Cited

FOREIGN PATENT DOCUMENTS

| WO | WO 01/94586 A2 | 12/2001 |
|---|---|---|
| WO | 02/08263 A2 | 1/2002 |
| WO | WO 02/062972 A | 8/2002 |
| WO | WO 03/068924 A | 8/2003 |
| WO | WO 2004/002526 A | 1/2004 |
| WO | 00/24913 A3 | 5/2004 |
| WO | WO 2008/091798 A2 | 7/2008 |

OTHER PUBLICATIONS

Grabmaier et al., "Molecular Cloning and Immunogenicity of renal cell carcinoma-assoicated antigen G250", Int. J. Cancer 85 (2000) 865-870.
Van Duk et al., "Induction of tumor-cell lysis by bi-specific monoclonal antibodies recognizing renal-cell carcinoma and cd3 antigen", Int. J. Cancer 43 (1989) 344-349. (Abstract).
Submission filed in the Canadian Patent Office for Canadian Serial No. 2,435,683 dated Sep. 11, 2008, 6 pages.
Choudhary et al., "Mutated Cytochrome b as a Determinant of a new Monoclonal Antobody . . . ", Int. J. Can. 82: 562-568, 1999.
Danen et al., "The Disintegrin Eristostatin Interferes with Integrin . . . ", Exp. Cell Res., 238: 188-196, 1998.
Blok et al., "A Bispecific Monoclonal Antibody Directed Against Both the Membrane-Bound Complement Regulator CD55 and the Renal Tumor Associated Antigen G250 Enhances C3 Deposition and Tumor Cell Lysis by Complement", J. Immunol. 1998; 160; 3437-3443.
Kranenborg et al., "Development and Characterization of Anti-Renal Cell Carcinoma X Antichelate Bispecific Monoclonal Antibodies for Two-Phase Targeting of Renal Cell Carcinoma", Cancer Research, 55: 5864s-5867S, 1995.
Simmons et al., "Expression of full-length immunoglobulins in *Escherichia coli*: rapid and efficient production of aglycosylated antibodes", Journal of Immunological Methods, 263(2002), 133-147.
Office Action issued in U.S. Appl. No. 11/655,110, Oct. 15, 2010, 20 pages.
Kinouchi et al., "Characterization of a Kidney Antigen Defined by a Mouse Monoclonal Antibody K2.7", The Journal of Urology, vol. 137, Jan. 1987, 151-154.
Chiou, Biodistribution and Radioimmunoscintigraphy Studies of Renal Cell Carcinoma using Tumor-Preferential Monoclonal Antibodies and F(ab') 2 Fragments, The Journal of Urology, vol. 142, Dec. 1989, 1584-1588.
Rachel et al., "Monoclonal Antibody 138H11 in Immunoscintigraphy of Human Kidney Tumors—In Vitro Results", Renal Cell Cancer, 1994, 66-68.
Finstad et al., "Specificity analysis of mouse monoclonal antibodies defining cell surface antigens of human renal cancer", Pro. Natl. Acad. Sci., vol. 82, pp. 2955-2959, May 1985.
Tokuyama et al., "Mouse Monoclonal Antibodies with Restricted Specificity for Human Renal Cell Carcinoma and Ability to Modulate the Tumor Cell Growth in Vitro", Hybridoma, vol. 7, No. 2, 1988, 155-165.
Vessella et al., "Monoclonal Antibodies in Urology: Review of Reactivities and Applications in Diagnosis, Staging, and Therapy", Seminars in Urology, vol. III, No. 2 May 1985, 158-167.
Yoshida et al., "Monoclonal Antibody to a Proximal Nephrogenic Renal Antigen: Immunohistochemical Analysis of Formalin-fixed, Paraffin-embedded Human Renal Cell Carcinomas", Cancer Research, 49, 1802-1809, Apr. 1, 1989.
E. Oosterwijk et al., "Monoclonal Antibody G250 Recognizes a Determinant Present in Renal Cell Carcinoma and Absent From Normal Kidney", International Journal of Cancer, 1986, vol. 38, pp. 489-494, XP008009792.
Weijtens et al, Int. J. Cancer, 1998, vol. 77, pp. 181-187 (Abstract).
Journal of Clinical Oncology, 1993, vol. 11, No. 4, p. 738-750.
Steffens et al., J. Clin. Oncol. 15 (1997), 1529-1537.
William E. Paul, Fundamental Immunology, 3rd ed., p. 242, 1993.

Gorter et al., Clinical Experimental Immunology, 87: 111-116, 1992.
Weijtens et al., "Single Chain IG/Y Gene-Redirected Human T Lymhocytes Produce Cytokines, Specifically Lyse tumor Cells, and Recycle Lytic Capacity", The Journal of Immunology, 1996,157: 836-843.
Velders et al., "New Chimeric Anti-Pancarcinoma Monoclonal Antibody with Superior cytotoxicity-mediating Potency", Cancer Research, vol. 54, Apr. 1, 1994, pp. 1753-1759.
Beck et al., "A phase I/II trial with monoclonal antibody WX-G250 in combination with low dose interleukin-2 in metastatic renal cell carcinoma," Proc. of the Am. Assoc. for Cancer Research Annual, 2002, p. 910, vol. 43.
Berenbaum, "Synergy, additivism and antagonism in immunosuppression. A critical review,"Clin. Exp. Immunol., 1997, pp. 1-18, vol. 28.
Bismar et al., "Quantification of G250 mRNA expression in renal epithelial neoplasms by real-time reverse transcription-PCR of dissected tissue from paraffin sections," Pathology, 2003, pp. 513-517, vol. 35, No. 6.
Boccon-Gibod, "Are non-steroidal anti-androgens appropriate as monotherapy in advance prostate cancer?," European Urology Clinical Paper, 1998, pp. 159-164, vol. 33.
Brouwers et al., "Pharmacokinetics and tumor target of 131I-labeled F(ab')2 fragments of the chimeric monoclonal antibody G250: preclinical and clinical pilot studies," Cancer Biotherapy and Radiopharmaceuticals, 2004, pp. 466-477, vol. 19, No. 4.
Buskens et al., "Adenocarcinomas of the gastroesophageal junction: a comparative study of the gastric cardia and the esophagus with respect to cyclogygenase-2 expression," Digestive Disease Week Abstracts and Itinerary Planner, vol. 2003, No. 850.
Castagneto et al., "Palliative and therapeutic activity of IL-2 immunotherapy in unresectable malignant pleural mesothelioma with pleural effusion: results of a phase II study on 31 consecutive patients," Lung Cancer, 2001, pp. 303-310, vol. 31, No. 2-3.
De-Jong Busnac et al., Ophthalmologic complications of low-dosage Tamoxifen in the treatment of breast carcinoma, PubMed—indexed for Medline, 1989. (Abstract only).
Dorner et al., "Successful treatment of prostatic cancer with orally active depot estrogen ethinylestradiol sulfonate (Turisteron)," Exp Clin Endocrinol, 1985, pp. 190-195, vol. 86, No. 2.
"Eine Neue Antikorpoer—Therapie fur Nierenzellkarzinome," Mar. 29, 2006, 3 pages, XP002374806, cited in U.S. Appl. No. 11/630,170.
Frost et al., "A Phase I/IB Trial of Murine Monoclonal Anti-GD2 Antibody 14.G2a plus Interleukin-2 in Children with Refractory Neuroblastoma," Cancer, 1997, pp. 317-333, vol. 80.
Hank et al., "Augmentation of antibody dependent cell mediated cytotoxicity following in vivo therapy with recombinant interleukin-2," Cancer Research 50, 1990, pp. 5234-5239.
Jongmans et al., "Targeting of adenovirus to human renal cell carcinoma cells," Urology, 2003, pp. 559-565, vol. 62, No. 3.
Kawata et al., "Immunological effect of recombinant interferon gamma in renal cell carcinoma," PubMed—indexed for Medline, Jun. 1993, pp. 511-515, vol. 29, No. 6. (Abstract only).
Kossman et al., "A Phase I Trial of Humanized Monoclonal Antibody HuM195 (anti-CD33) with Low-Dose Interleukin 2 in Acute Myelogenous Leukemia," Clin Cancer Res, 1999, pp. 2748-2755, vol. 5.
Liu et al., "Anti-renal cell carcinoma chimeric antibody G250: cytokine enhancement of in vitro antibody-dependent cellular cytotoxicity," Cancer Immunol Ammunother, 2002, pp. 171-177, vol. 51, No. 3.
Margolin, "Interleukin-2 in the treatment of renal cancer," Seminars in Oncology, 2002, pp. 194-203, vol. 27, No. 2.
Moch et al., "Genetic aberrations detected by comparative genomic hybridization are associated with clinical outcome of renal cell carcinoma," Cancer Research, 1996, pp. 27-30, vol. 56.
Mulders, et al., "The role of adjuvant immunotherapy in renal cell carcinoma," Current Urology Reports, 2002, pp. 44-49, vol. 3.
Nasi et al., "Treatment with daily low-dose subcutaneous interleukin-2 followed by monoclonal antibody R24 against GD3

(56) References Cited

OTHER PUBLICATIONS ganglioside in patients with metastatic melanoma," http://www.asco.org/prof/me/html/abstracts/ms/m_1770.htm, 1997.

Pavone, "Long-term treatment with low doses of interleukin-2 and interferon-a: immunological effects in advanced renal cell cancer," Cancer Immunol. Immunother., 2001, pp. 82-86, vol. 50.

Saarnio et al., "Transmembrane carbonic anhydrase, MN/CA IX, is a potential biomarker for biliary tumours," Journal of Hepatology 35, 2001, pp. 643-649.

Smith, Kendall A., "Lowest dose interleukin-2 immunotherapy," Blood, 1993, pp. 1414-1423, vol. 81, No. 6.

Son et al., "Dendritic cells pulsed with apoptotic squamous cell carcinoma have anti-tumor effects when combined with interleukin-2," The Laryngoscope, 2001, pp. 1472-1478, vol. 111, No. 8.

Sondel et al. "Clinical and Immunological effects of recombinant interleukin-2 given by repetitive weekly cycles to patients with cancer," Cancer Research 48, 1988, pp. 2561-2567.

Sosman et al., "Repetitive weekly cycles of interleukin2. II. Clinical Immunologic effects of dose, schedule, and addition of indomethacin," Journal of the National Cancer Institute, 1988, pp. 1451-1461, vol. 80, No. 18.

Steffens et al., "Phase I radioimmunotherapy of metastatic renal cell carcinoma with 131I-labeled chimeric monoclonal antibody G250," Clinical Cancer Research, 1999, 3268S-3274S, vol. 56.

Stein et al., "The clinical effects of prolonged treatment of patients with advanced cancer with low-dose subcutaneous interleukin-2," Br. J. Cancer 63, 1991, pp. 275-278.

Turner et al., "MN antigen expression in normal, preneoplastic, and neoplastic esophagus: a clinicopathological study of a new cancer-associated biomarker," Hum. Pathol. Jun. 1997: 28(6):740-4.

Uemura et al., "Effects of MAbG250 and anti-idiotyeantibody based immunotherapy in renal cell carcinoma," Biotherapy, 1997, pp. 400-403, vol. 11, No. 3.

Uemura et al., "MN/CA IX/G250 as a potential target for immunotherapy of renal cell carcinomas," British Journal of Cancer, 1999, 81(4) pp. 741-746.

Ullrich et al., "A phase I/II trial with monoclonal antibody WX-G250 in combination with low dose interleukin-2 in metastatic renal cell carcinoma," Proc Am Soc Clin Oncol 22: 2003 ASCO Annual Meeting (abstr 692).

Van Dijk et al., "Therapeutic effects of monoclonal antibody G250, interferons and tumor necrosis factor, in mice with renal cell carcinoma xenografts," International Journal of Cancer, 1994, pp. 262-268, vol. 56, No. 2.

Varga et al., "A prospective open-label single-arm phase II study of chimeric monoclonal antibody cG250 in advanced renal cell carcinoma patients," Folia Biologica (Prague), 2003, pp. 74-77, vol. 49, No. 2.

Vissers et al., "The renal cell carcinoma-associated antigen G250 encodes a human leukocyte antigen-A2.1-restricted epitope recognized by cytotoxic T lymphocytes," Cancer Research 59, 1999, pp. 5554-4449.

Wiesenthal, "Human tumor assay journal," http://weisenthal.org/synergy1.htm, 2008.

"Information for Authors," The Journal of Immunology, 1996, 1 page.

"Author Guidelines," Clinical & Experimental Immunology: The Journal of Translational Immunology, Dec. 1, 2009, 12 pages.

Liu Zhanqi et al: "Anti-renal cell carcinoma chimeric antibody G250: Cytokine enhancement of in vitro antibody-dependent cellular cytotoxicity" Cancer Immunology Immunotherapy, vol. 51, No. 3, May 2002 (May 2002), pp. 171-177, XP001172419 ISSN: 0340-7004.

Bleumer Ivar et al: "A phase I/II trial with chimeric monoclonal antibody WX-G250 in combination with low-dose interleukin-2 for patients with metastatic renal cell carcinoma." Journal of Urology, vol. 169, No. 4 Supplement, Apr. 2003 (Apr. 2003), p. 261, XP008023419 98th Annual Meeting of the American Urological Association (AUA);Chicago, IL, USA; Apr. 26-May 2, 2003 ISSN: 0022-5347.

\* cited by examiner

Figure 1A

VH G250 (nucleotide SEQ ID NO:1; amino acid SEQ ID NO:2)

```
1/1                                          31/11
gac gtg aag ctc gtg gag tct ggg gga ggc tta gtg aag ctt gga ggg tcc ctg aaa ctc
 D   V   K   L   V   E   S   G   G   G   L   V   K   L   G   G   S   L   K   L 61/21                                        91/31
tcc tgt gca gcc tct gga ttc act ttc agt aac tat tac atg tct tgg gtt cgc cag act
 S   C   A   A   S   G   F   T   F   S   N   Y   Y   M   S   W   V   R   Q   T
                                             ─────H1─────

121/41                                       151/51
cca gag aag agg ctg gag ttg gtc gca gcc att aat agt gat ggt ggt atc acc tac tat
 P   E   K   R   L   E   L   V   A   A   I   N   S   D   G   G   I   T   Y   Y
                                        ──────────────H2──────────────

181/61                                       211/71
cta gac act gtg aag ggc cga ttc acc att tca aga gac aat gcc aag aac acc ctg tac
 L   D   T   V   K   G   R   F   T   I   S   R   D   N   A   K   N   T   L   Y
 ─────H2──────

241/81                                       271/91
ctg caa atg agc agt ctg aag tct gag gac aca gcc ttg ttt tac tgt gca aga cac cgc
 L   Q   M   S   S   L   K   S   E   D   T   A   L   F   Y   C   A   R   H   R 301/101                                      331/111
tcg ggc tac ttt tct atg gac tac tgg ggt caa gga acc tca gtc acc gtc tcc tca
 S   G   Y   F   S   M   D   Y   W   G   Q   G   T   S   V   T   V   S   S
 ──────────H3──────────
```

Figure 1B

VL G250 (nucleotide SEQ ID NO:3; amino acid SEQ ID NO:4)

```
1/1
gac att gtg atg acc cag tct caa aga ttc atg tcc aca aca gta gga gac agg gtc agc
 D   I   V   M   T   Q   S   Q   R   F   M   S   T   T   V   G   D   R   V   S 61/21                                   31/11
atc acc tgc aag gcc agt cag aat gtg gtt tct gct gtt gcc tgg tat caa cag aaa cca
 I   T   C   K   A   S   Q   N   V   V   S   A   V   A   W   Y   Q   Q   K   P
                         ─────────────L1─────────────

121/41                                  91/31
gga caa tct cct aaa cta ctg att tac tca gca tcc aat cgg tac act gga gtc cct gat
 G   Q   S   P   K   L   L   I   Y   S   A   S   N   R   Y   T   G   V   P   D
                                   ──────────L2──────────

181/61                                  151/51
cgc ttc aca ggc agt gga tct ggg aca gat ttc act ctc acc att agc aat atg cag tct
 R   F   T   G   S   G   S   G   T   D   F   T   L   T   I   S   N   M   Q   S 241/81                                  211/71
gaa gac ctg gct gat ttt ttc tgt caa caa tat agc aac tat ccg tgg acg ttc ggt gga
 E   D   L   A   D   F   F   C   Q   Q   Y   S   N   Y   P   W   T   F   G   G
                         ─────────────L3─────────────

301/101                                 271/91
ggc acc aag ctg gaa atc aaa
 G   T   K   L   E   I   K
```

CDRs: H1, H2, H3 & L1, L2, L3
CDR definition according to Kabat scheme

SEQUENCE LISTING

```
<160> NUMBER OF SEQ ID NOS: 4

<210> SEQ ID NO 1
<211> LENGTH: 357
<212> TYPE: DNA
<213> ORGANISM: Artificial Sequence
<220> FEATURE:
<223> OTHER INFORMATION: mouse/human chimeric antibody gene
<220> FEATURE:
<221> NAME/KEY: misc_feature
<222> LOCATION: (91)..(105)
<223> OTHER INFORMATION: sequence coding for the complementary
      determining region
<220> FEATURE:
<221> NAME/KEY: misc_feature
<222> LOCATION: (148)..(198)
<223> OTHER INFORMATION: sequence coding for the complementary
      determining region
<220> FEATURE:
<221> NAME/KEY: misc_feature
<222> LOCATION: (295)..(324)
<223> OTHER INFORMATION: sequence coding for the complementary
      determining region

<400> SEQUENCE: 1
gacgtgaagc tcgtggagtc tgggggaggc ttagtgaagc ttggagggtc cctgaaactc        60
tcctgtgcag cctctggatt cactttcagt aactattaca tgtcttgggt tcgccagact       120
ccagagaaga ggctggagtt ggtcgcagcc attaatagtg atggtggtat cacctactat       180
ctagacactg tgaagggccg attcaccatt tcaagagaca atgccaagaa caccctgtac       240
ctgcaaatga gcagtctgaa gtctgaggac acagccttgt tttactgtgc aagacaccgc       300
tcgggctact tttctatgga ctactgggt caaggaacct cagtcaccgt ctcctca          357

<210> SEQ ID NO 2
<211> LENGTH: 119
<212> TYPE: PRT
<213> ORGANISM: Artificial Sequence
<220> FEATURE:
<223> OTHER INFORMATION: mouse/human chimeric antibody

<400> SEQUENCE: 2

Asp Val Lys Leu Val Glu Ser Gly Gly Gly Leu Val Lys Leu Gly Gly
1               5                   10                  15

Ser Leu Lys Leu Ser Cys Ala Ala Ser Gly Phe Thr Phe Ser Asn Tyr
            20                  25                  30
```

Tyr Met Ser Trp Val Arg Gln Thr Pro Glu Lys Arg Leu Glu Leu Val
            35                  40                  45

Ala Ala Ile Asn Ser Asp Gly Gly Ile Thr Tyr Tyr Leu Asp Thr Val
 50                  55                  60

Lys Gly Arg Phe Thr Ile Ser Arg Asp Asn Ala Lys Asn Thr Leu Tyr
 65                  70                  75                  80

Leu Gln Met Ser Ser Leu Lys Ser Glu Asp Thr Ala Leu Phe Tyr Cys
                 85                  90                  95

Ala Arg His Arg Ser Gly Tyr Phe Ser Met Asp Tyr Trp Gly Gln Gly
            100                 105                 110

Thr Ser Val Thr Val Ser Ser
        115

<210> SEQ ID NO 3
<211> LENGTH: 321
<212> TYPE: DNA
<213> ORGANISM: Artificial Sequence
<220> FEATURE:
<223> OTHER INFORMATION: mouse/human chimeric antibody gene
<220> FEATURE:
<221> NAME/KEY: misc_feature
<222> LOCATION: (70)..(102)
<223> OTHER INFORMATION: sequence coding for the complementary
      determining region
<220> FEATURE:
<221> NAME/KEY: misc_feature
<222> LOCATION: (148)..(168)
<223> OTHER INFORMATION: sequence coding for the complementary
      determining region
<220> FEATURE:
<221> NAME/KEY: misc_feature
<222> LOCATION: (265)..(291)
<223> OTHER INFORMATION: sequence coding for the complementary
      determining region

<400> SEQUENCE: 3
gacattgtga tgacccagtc tcaaagattc atgtccacaa cagtaggaga cagggtcagc      60
atcacctgca aggccagtca gaatgtggtt tctgctgttg cctggtatca acagaaacca    120
ggacaatctc ctaaactact gatttactca gcatccaatc ggtacactgg agtccctgat    180
cgcttcacag gcagtggatc tgggacagat ttcactctca ccattagcaa tatgcagtct    240
gaagacctgg ctgatttttt ctgtcaacaa tatagcaact atccgtggac gttcggtgga    300
ggcaccaagc tggaaatcaa a                                              321

<210> SEQ ID NO 4
<211> LENGTH: 107
<212> TYPE: PRT
<213> ORGANISM: Artificial Sequence
<220> FEATURE:
<223> OTHER INFORMATION: mouse/human chimeric antibody

<400> SEQUENCE: 4

Asp Ile Val Met Thr Gln Ser Gln Arg Phe Met Ser Thr Thr Val Gly
 1               5                  10                  15

Asp Arg Val Ser Ile Thr Cys Lys Ala Ser Gln Asn Val Val Ser Ala
                 20                  25                  30

Val Ala Trp Tyr Gln Gln Lys Pro Gly Gln Ser Pro Lys Leu Leu Ile
             35                  40                  45

Tyr Ser Ala Ser Asn Arg Tyr Thr Gly Val Pro Asp Arg Phe Thr Gly
 50                  55                  60

Ser Gly Ser Gly Thr Asp Phe Thr Leu Thr Ile Ser Asn Met Gln Ser
 65                  70                  75                  80

```
Glu Asp Leu Ala Asp Phe Phe Cys Gln Gln Tyr Ser Asn Tyr Pro Trp
                85                  90                  95
Thr Phe Gly Gly Gly Thr Lys Leu Glu Ile Lys
            100             105
```

HYBRIDOMA CELL LINE G250 AND ITS USE FOR PRODUCING MONOCLONAL ANTIBODIES

CROSS REFERENCE TO RELATED APPLICATION

This application is a divisional application of U.S. application Ser. No. 11/655,110, filed Jan. 19, 2007, now abandoned, which is a continuation application of U.S. application Ser. No. 10/470,940, filed Aug. 5, 2003, now abandoned, which is a 371 of International Application No. PCT/EP02/01282, filed Feb. 7, 2002, and designating the U.S., which claims the benefit under 35 USC §119(e) of U.S. Provisional Applications 60/266,853, filed Feb. 7, 2001, and 60/327,008, filed Oct. 5, 2001.

DESCRIPTION

The invention relates to the hybridoma cell G250 or any progeny cell thereof capable of producing G250 antibody.

The fusion of mouse myeloma cells with the spleen cells from immunized mice, first described by Kohler and Milstein, Nature, 256, 495-997 (1975), makes it possible to obtain continuous cell lines which produce homogeneous antibodies, referred to as monoclonal antibodies (mAb).

Many examples exist where hybrid cells or hybridomas are described. These hybridomas are used to produce antibodies useful for various scientific investigations (Current Topics in Microbiology and Immunology, volume 81—"Lymphocyte Hybridomas", F. Melchers et al., Springer-Verlag (1978) and references therein; C. J. Barnstable et al., Cell, (1978), 14, 9-20; P. Parham, W. F. Bodmer, Nature (1978), 276, 397-399; Handbook of Experimental Immunology, 3rd edition, vol. 2, D. M. Wier, editor, Blackwell, 1978, Chapter 25, Chem. Eng. News, 15-17 (1979); Kennett, R. H., McKearn, J. T., and Bechtol, K. B. (1980) Monoclonal Antibodies. Hybridomas: A New Dimension in Biological Analysis (Plenum, N.Y.)). These reports describe the principal techniques for the production of monoclonal antibodies by hybridomas.

The monoclonal antibody G250, subclass IgG1, recognizes an antigen preferentially expressed on membranes of renal cell carcinoma cells (RCC) and not expressed in normal proximal tubular epithelium. The antibody G250 was obtained by immunizing a mouse with cell homogenates from primary RCC lesions obtained from different patients (Oosterwijk et al., Int. J. Cancer 38 (1986), 489-494).

The monoclonal antibody G250 as well as chimeric derivatives thereof have been used in clinical studies (Steffens et al., J. Clin. Oncol. 15 (1997), 1529-1537). The nucleic acid sequence coding for the antigen-binding site of G250 is subject matter of co-pending U.S. application Ser. No. 60/266,853, which is herein incorporated by reference.

The production of a hybridoma cell line expressing G250 antibody was generally described in the international patent application WO88/08854 and Oosterwijk et al. (supra). As stated above, a cell homogenate from primary RCC lesions obtained from different patients and thus an unspecific material was used as an immunogen. Furthermore, the hybridoma cell line had not been deposited with a recognized depository institution according to the Budapest Treaty. Thus, an exact reproduction of the G250 hybridoma cell line from the publically available prior art documents does not seem to be possible.

Meanwhile it has been found that the G250 antibody binds to the so-called MN antigen which is described e.g. in WO93/18152. The G250 binding site on the MN antigen is, however, not known at present. Moreover, recent results show that the G250 binding site is a conformational epitope which further increases the burden to reproduce the G250 hybridoma cell line, since no specified epitope sequence on the MN antigen which binds to G250 can be provided.

Thus, the present invention relates to a hybridoma cell capable of producing a G250 monoclonal antibody. This hybridoma cell was deposited under the Budapest Treaty for the Deposit of Microorganisms on Sep. 11, 2001 at Deutsche Sammlung von Mikroorganismen und Zellkulturen GmbH (DSMZ), Mascheroder Weg 1b, 38124 Braunschweig, Germany under the Accession Number DSM ACC 2526. The deposit is the first publically available disclosure of a G250 antibody producing hybridoma cell line.

A further aspect of the invention is a progeny cell derived from said hybridoma DSM ACC 2526 which produces a G250 antibody.

In a preferred embodiment, the present invention relates to a progeny cell of the deposited hybridoma cell producing a G250 antibody wherein the progeny cell is obtained by recombinant DNA methods, e.g. by transferring genetic material encoding the G250 antibody or at least the antigen-binding site thereof into a receptor cell. The genetic material may be directly or indirectly obtained from the deposited hybridoma cell G250. "Directly obtained" means that the G250 genetic material is derived from the deposited hybridoma cell. "Indirectly obtained" means that the G250 genetic material is derived from an already existing G250 progeny cell or from other sources including chemical synthesis.

Preferably the G250 genetic material comprises nucleotide sequences encoding at least the G250 antigen-binding site, particularly nucleotide sequences encoding the complementary determining regions CDR3, CDR2 and/or CDR1 of the heavy chain antigen-binding site [nucleotide SEQ ID NO:1; amino acid SEQ ID NO:2] as shown in FIG. 1A (designated H1-H3) and/or the complementary determining regions CDR3, CDR2 and/or CDR1 of the light chain antigen-binding site [nucleotide SEQ ID NO:3; amino acid SEQ ID NO:4] (designated L1-L3) as shown in FIG. 1B.

According to the invention the term "G250 antibody" covers any antibody including multispecific antibodies (e.g. bispecific antibodies) and antibody fragments as long as they exhibit the desired activity, i.e. at least one G250 antigen-binding site. The antibody may be an IgM, IgG (e.g. $IgG_1$, $IgG_2$, $IgG_3$ or $IgG_4$), IgD, IgA or IgE, particularly IgG antibody, a recombinant antibody or an antibody fragment obtained by proteolytic methods or by recombinant DNA methods.

The term "monoclonal antibody" as used herein refers to an antibody obtained from a population of substantially homogeneous antibodies, i.e., the individual antibodies comprising the population are identical, except for possibly naturally occurring mutations that may be present in minor amounts.

The term "antibody" as used herein refers to any polypeptide containing at least one G250 antigen-binding site, i.e. at least the CDR3 region of the G250 heavy chain and/or the CDR3 region of the G250 light chain or a variant G250 CDR3 region having an identity of at least 80%, preferably at least 90% to the original G250 CDR3 region on the amino acid level, provided that the variant CDR3 region has equivalent antigen-binding characteristics, particularly affinity and specificity compared to the original CDR3 region.

Preferably, the term "antibody" herein includes chimeric antibodies, humanized and fully humanized antibodies, single chain antibodies, e.g. sFv antibody fragments, diabody fragments, proteolytic or recombinant antibody fragments such as Fv-, Fab-, Fab'- or F(ab')$_2$-fragments or other antigen-binding subsequences of antibodies. The antibody may also be a fusion or a conjugate with other entities.

The antibodies herein specifically include chimeric antibodies in which a portion of the heavy and/or light chain including the antigen-binding site is identical with or homologous to corresponding sequences derived from the original hybridoma cell line G250, while the remainder of the chains is identical with or homologous to corresponding sequences derived from other species or belonging to another antibody class or subclass as well as fragments of such antibodies as long as they exhibit the desired biological activity. More preferably, the chimeric antibody comprises variable regions, e.g. the complement-determining regions (CDRs) and and the framework regions from the heavy chain and the light chain of the original G250 monoclonal antibody and constant human sequences, particularly constant human kappa light chain and gamma heavy chain sequences. The manufacture of chimeric antibodies is described e.g. by Morrison et al. (Proc. Natl. Acad. Sci. USA 81 (1984), 6851-6855), which is herein incorporated by reference.

Further, antibody herein specifically includes humanized antibodies or fully human antibodies. Humanized antibodies are immunoglobulins, immunoglobulin chains or fragments thereof which contain minimal sequence derived from non-human immunoglobulin. More particularly, humanized antibodies are human immunoglobulins in which residues from a CDR of a given human antibody are replaced by residues from the G250 CDR, particularly the CDR1, 2 and/or 3 region of the heavy and/or light chain. Furthermore, humanized antibodies may comprise residues which are found neither in the recipient human antibody, nor in the imported G250 CDR sequences. These modifications are made to further refine and optimize antibody performance. In general, the humanized or fully human antibody will comprise substantially all of at least 1, and typically 2, variable domains, in which all or substantially all of the CDR regions correspond to those of the original G250 immunoglobulin and all or substantially all of the framework regions and constant regions are those of a human immunoglobulin sequence. The manufacture of humanized antibodies is described, e.g. in Jones et al. (Nature 321 (1986), 522-525), Riechmann et al. (Nature 332 (1988), 323-329 and Presta (Curr. Op. Struct. Biol. 2 (1992), 332-339), which are herein incorporated by reference.

Further, antibodies specifically include single-chain antibodies such as single-chain Fv antibody fragments comprising the VH and VL domains of an antibody, wherein these domains are present in a single polypeptide chain. Generally, the Fv polypeptide further comprises a polypeptide linker between the VH and VL domains which enables the sFv to form the desired structure for antigen binding. The manufacture of sFv antibodies is described e.g. by Pluckthun in: The Pharmacology of Monoclonal Antibodies, Vol. 113, Rosenburg and Moore, Eds., Springer Verlag, N.Y., pp. 269-315 (1994), Barbas III (Methods: Companion Methods Enzymol. 2 (1991), 119) and Hoogenboom et al. (Immunol. Rev. 130 (1992), 41-68), which are herein incorporated by reference.

Further, antibodies specifically include diabodies, i.e small antibody fragments with two antigen-binding sites, which fragments comprise a heavy chain variable domain connected to a light chain variable domain in the same polypeptide chain. By using a linker that is too short to allow pairing between the two domains on the same chain, the domains are forced to pair with the complementary domains of another chain and create two antigen binding sites. The manufacture of diabodies is described e.g. by Hollinger et al., (Proc. Natl. Acad. Sci. USA 90 (1993), 6444-6448), which is herein incorporated by reference.

Further, antibodies specifically include multispecific antibodies e.g. heterobispecific antibodies comprising at least one G250 antigen-binding site and the antigen-binding site from a different antibody, e.g. an anti-CD3-antibody.

The antibody produced by the G250 hybridoma cell or a progeny cell thereof may be fused or coupled to a marker or effector component. For example, the G250 antibody may be recombinantly modified so that it is linked to cytokines such as interleukin-2 (IL-2), tumor necrosis factor (TNF) and/or granulocyte macrophage colony stimulating factor (GM-CSF).

Furthermore, the G250 antibody may be conjugated, e.g. by covalent coupling or fused to a suitable marker group, e.g. a fluorescent group, a radioactive marker group etc. or a cytotoxic agent including radioactive isotopes such as I, Y, Pr, Tm, In, such as $^{123}$I, $^{125}$I, $^{135}$I, $^{99m}$Tm or $^{111}$In, chemotherapeutic agents and toxins such as enzymatically active toxins of bacterial, fungal, plant or animal origin, or fragments thereof.

The receptor cell into which G250 specific genetic material from the original G250 hybridoma cell or any progeny thereof or of synthetic origin is transferred may be any suitable host cell capable of expressing antibodies. For example, the host cell maybe a prokaryotic cell, preferably an *E. coli* cell or a eukaryotic cell. Preferred eukaryotic cells are e.g. insect, yeast and mammalian cells. Most preferred host cells are mammalian cells, e.g. human or mouse myeloma cells or CHO-cells.

Further, the present invention comprises a method of producing G250 antibody or derivatives thereof comprising: cultivating a G250 hybridoma cell or a progeny cell thereof under suitable conditions, wherein a G250 antibody is produced and obtaining the antibody and/or derivative thereof from the cell and/or from the cell culture medium.

The antibody obtained according to this method is particularly useful for producing pharmaceutical formulations which comprise the antibody as an active agent, besides pharmaceutically acceptable carriers, diluents and/or adjuvants.

In an especially preferred embodiment, the active agent is a chimeric G250 antibody which may be present as such or as a conjugate with a radioactive group, e.g. with $^{123}$I, $^{125}$I, $^{131}$I, $^{99m}$Tm or $^{111}$In.

Further, the present invention relates to the use of the deposited hybridoma cell and progeny cells thereof for manufacturing G250 antibodies as described above, e.g. monoclonal antibodies, chimeric antibodies, humanized antibodies, fully humanized antibodies, bispecific antibodies and antibody fragments such as (Fab')$_2$-, Fab'-, Fab- and Fv-fragments.

The chimeric G250 antibody was successfully used in clinical studies for the treatment of renal cell carcinoma patients after surgery. Even the study has not yet been completed, the treated patients already show a significant increase in median survival (more than 15 months) compared to untreated patients (three months) or patients treated with standard therapy (10-12 months).

Surprisingly, it was found that in some cases tumor regression occurred more than six months after start of therapy. Thus, chimeric G250 antibody and other G250 antibodies are capable of eliciting a delayed immune response in cancer therapy, preferably in the treatment of renal cell carcinoma and more preferably for the treatment of metastases after tumor surgery.

BRIEF DESCRIPTION OF THE DRAWING

FIG. 1A shows nucleotide sequences encoding the complementary determining regions CDR3, CDR2 and CDR 1 (designated H1-H3) of the heavy chain antigen-binding site (nucleotide SEQ ID NO: 1; amino acid SEQ ID NO:2), and FIG. 1B shows the complementary determining regions CDR3, CDR2 and CDR 1 (designated L1-L3) of the light chain antigen-binding site (nucleotide SEQ ID NO:3; amino acid SEQ ID NO:4).

EXAMPLE 1

Deposit of the G250 Hybridoma Cell Line

The G250 hybridoma cell line was produced as described in Example 1 of WO88/08854. Therein a general immunization protocol is given. Further informations, e.g. a molecular characterization of the G250 antibody and the G250 hybridoma cell are lacking.

The G250 hybridoma cell line was deposited according to the requirements of the Budapest Treaty at DSMZ under the accession No. DSM ACC 2526 on Sep. 11, 2001.

EXAMPLE 2

Mapping of the Epitope Recognized by Monoclonal Antibody G250

From collective experimental evidence it is assumed that the G250 protein epitope recognized by monoclonal antibody G250 (MAbG250) is conformational, most likely of a non-linear nature. This assumption is based on the following observations:

MabG250 does not react with antigen G250 in Western blot analysis

Purification of G250 antigen by MAbG250 affinity chromatography is highly inefficient, with efficiencies decreasing with increased time needed to perform the purification, suggesting rapid degradation/unfolding of the G250 epitope, in spite of optimal conditions to prevent proteolysis.

Addition of detergents in general lead to decreased G250 detection levels in ELISA Truncation of the cDNA encoding for G250 antigen, followed by transient transfection in G250-negative cells, followed by immunohistochemical analysis revealed:

| cDNA construct | G250-reactivity |
|---|---|
| nt 1-1500 (aa 1-459), complete protein | + |
| nt 1-1218 (aa 1-406), G250 without transmembrane region | +/− |
| nt 1-1074 (aa 1-358) | − |
| nt 1-843 (aa 1-281) | − |
| nt 1-672 (aa 1-224) | − |
| nt 1-450 (aa 1-150) | − |

It was found that G250-reactivity was lost, even when large CDNA constructs were used.

To further delineate the G250 epitope, the NovaTope system (Novagen Inc.) was used, a system which ensures expression of all constructs ligated into this vector, i.e., all possible fragments are expressed, irrespective of reading frame. This allows identification of epitopes present in the middle part of a protein.

The cDNA encoding for the MN (G250) antigen was digested with DNAse I for 2 hours, resulting in fragments of approximately 50-200 nucleotides encoding polypeptides having a length of about 15-70 amino acids. After dA tailing, the fragments were inserted into the pScreen T vector, and the ligation mixture was added to competent *E. coli* DE3 bacteria for transformation. Bacteria were plated on selection plates. Bacterial clones were blotted onto nitrocellulose filters and screened with G250 antibody. In total 7 colonies were identified with MAbG250. G250 reactivity was weak. After further re-screening, only one bacterial clone appeared to react with MAbG250, albeit extraordinary very weak, and most likely due to background staining. Sequence analysis of the clone did not reveal any G250-sequences, but showed the presence of a truncated vector. Thus, the staining of the nitrocellulose blot was most likely the result of non-specific background.

In a further experiment, cDNA encoding the MN (G250) antigen was digested with DNAse I, but now fragments of 200-600 nucleotides, encoding polypeptides of approximately 65-200 amino acids were isolated and cloned into the expression vector and expressed in bacteria. Separate bacterial colonies were screened for G250 reactivity.

Reactivity with G250 was not apparent. Blots were stained for extended times, after which a faint staining was observed with 6 bacterial isolates. The bacterial isolates only contained a truncated vector and an unrelated sequence.

Thus, no partial sequence of the MN antigen having strong reactivity with MAbG250 could be identified.

These results strongly suggest that the G250 epitope is conformational epitope. Further, the G250 epitope on the MN antigen cannot be characterized by conventional methods even with considerable efforts.

EXAMPLE 3

Development of a Chimeric G250 IgG Production Cell Line

General Strategy

In order to construct a mouse/human chimeric version of the murine G250 antibody, the variable region genes for the heavy and light chains, which determine the binding specificity of the antibody, were cloned from the G250 murine hybridoma and assembled in vitro with human constant region genes to generate mouse/human chimeric antibody genes. Expression of these chimeric genes in the appropriate cell line resulted in production of a chimeric antibody with the same binding characteristics as the original murine antibody, but with approximately 75% of the molecule comprising human sequences.

The strategy for cloning the variable regions for the heavy and light chain genes from the G250 hybridoma was based upon the linkage in the genome between the variable region and the corresponding J (joining) region for functionally rearranged (and expressed) immunoglobulin genes. J region DNA probes can be used to screen genomic libraries to isolate DNA linked to the J regions; DNA in the germline configuration (unrearranged) would also hybridize to J probes, but is not linked to a variable region sequence and can be identified by restriction enzyme analysis enzyme analysis of the isolated clones.

The cloning strategy, therefore, was to isolate variable regions from rearranged heavy and light chain genes using JH and JK probes. In addition, to assist in identifying and characterizing the correct genomic clones, cDNA clones corresponding to the heavy and light chain variable regions were also obtained from the mRNA produced in the G250 hybridoma. Those genomic clones that matched the G250 cDNA sequences were cloned into expression vectors containing human constant regions and transfected into mouse myeloma cells to determine if an antibody was produced. The antibody from producing cells was then tested for binding specificity compared to the murine G250 antibody.

Cloning of G250 VH and VL cDNA

Total RNA was isolated from G250 hybridoma cell and used to generate specific VH and VL cDNA clones. First strand cDNA synthesis was performed using oligonucleotide primers specific for the murine kappa and IgG constant regions. After dG tailing, second strand synthesis was performed using C-tailed oligonucleotide primers. The heavy and light chain variable regions were amplified via polymerase chain reaction using specific 5' and 3' primers, and the amplification products were cloned into the plasmid vector pUC19. VH and VL clones were subjected to DNA sequence analysis to establish the base sequences of the putative G250 heavy and light chain variable regions. The sequencing results are shown in FIG. 1.

Cloning of the G250 Variable Region Genes:

To clone the variable region genes, high molecular weight genomic DNA was isolated from G250 hybridoma cells by treatment of isolated nuclei with SDS and proteinase K followed by two phenol extractions and an ethanol precipitation.

Southern blot analysis using a J region probe for the heavy chain locus suggested that the G250 heavy chain was contained on a 2.3 kilobase (Kb) Eco RI DNA fragment. Accordingly, the Eco RI fragments from hybridoma DNA were fractionated on a 0.8% agarose gel and the size range of approximately 2-3 Kb fragments was eluted from the gel and ligated to the vector arms of the lambda bacteriophage vector Zap II (Stratagene, La Jolla Calif., USA). The ligation was packaged into phage particles in vitro using Gigapack Gold (Stratagene) and plated on E. coli LE392 cells at a density of approximately 20.000 plaques per 150 mm plate. The plaques were transferred to nitrocellulose filters and probed with a $^{32}$P-labeled DNA probe (a 2.0 Kb Eco RI-BamHI fragment containing the murine J3 and J4 exons).

For the light chain G250 variable region gene, a Southern blot analysis using a murine J region probe from the kappa locus indicated that the correct gene was located on a 5.5 Kb Hind II fragment. Accordingly, G250 hybridoma DNA was digested with Hind II and DNA fragments of 5-6 Kb were isolated from a 0.8% agarose gel and ligated to the arms of the bacteriophage lambda vector Charon 27. The ligated DNA was packaged into phage particles in vitro using Gigapack Gold (Stratagene), and plated on E. coli LE392 cells at a density of approximately 20.000 plaques per 150 mm plate. The plaques were transferred to nitrocellulose filters and probed with a $^{32}$P-labeled DNA probe (a 2.7 Kb Hind II fragment containing all five J kappa exons).

Positive clones for the heavy and light chain genes were isolated following at least 3 rounds of plaque purification using the J region probes to verify hybridization to the phage DNA at each stage of purification. Purified DNA from the isolated phage clones for the heavy and light chain genes was digested with EcoRI (heavy chain) or Hind II (light chain) and fractionated on agarose gels. The appropriate size fragments (2.3 Kb for the heavy chain and 5.5 Kb for the light chain) were isolated from the gels, and subcloned into the plasmid vector pUC 19. These subcloned DNA fragments were shown by restriction endonuclease mapping and DNA sequence analysis to contain variable region antibody genes that matched the structures of the cDNA clones originally obtained from the G250 hybridoma.

Expression Plasmids

The 2.3 Kb Eco RI heavy chain variable region fragment was cloned into a suitable expression vector which contains the human G1 constant region and a gene which confers resistance to a selectable marker in mammalian cells. The 5.5. Kb HindIII light chain fragment was cloned into a suitable expression vector which contains the human kappa constant region and a gene conferring resistance to a selectable marker in mammalian cells. The presence of the cloned fragments and their orientation in the expression vectors was determined by restriction enzyme mapping. The basic vectors have been used previously for the construction of chimeric antibodies (Sun, L. et al., (1987) PNAS 84, p. 214; Knight et al., (1993), Molecular Immunology 30, p. 1443-1453). Expression of the chimeric antibody genes is achieved using the natural immunoglobulin promoters present upstream of the cloned variable regions; downstream regulatory signals are provided by the elements associated with the constant region genes.

Expression of the G250 Chimeric Antibody

The heavy and light chain expression vectors were used to co-transfect a non-producing mouse myeloma cell line using the technique of electroporation. An ELISA assay was used to screen clones for secreted antibody containing a human Fc region, and the highest producer (cG250) was chosen for further characterization.

The chimeric antibody was purified by chromatography on protein A-sepharose, and analyzed in a competition assay to verify that the antibody has the correct specificity. The cG250 antibody was found to be equally effective in competing with $^{125}$I-labelled murine G250 for binding to A704 renal cell carcinoma cells (which express the G250 antigen) as the unlabeled murine G250 antibody. The chimeric G250 antibody, therefore, is similar in its binding characteristics to the original murine G250 antibody.

EXAMPLE 4

Use of Chimeric G250 Antibody in a Clinical Study

Administration Protocol

Renal cell carcinoma patients, having metastases after surgery, were treated by administering 50 mg chimeric G250 antibody via 30 min. infusion once per week for 12 weeks.

Efficacy Conclusions:

In the present study durable stable disease for over six months was achieved in eight out of 32 patients (25%) of the patients. The median time to progression for all patients was 16 weeks (mean 26, 67 weeks) with a range from 4 to 70 weeks. As of December 2001, the date of cut off, five patients are still free of progression (51+, 56+, 60+, 64+, and 70+ weeks).

The importance of these findings is supported by the fact that most of these patients had documented progressive disease, for another two patients it is assumed that they were progressive at study entry. In addition, three of these patients were refractory to prior cytokine and chemotherapy or had relapsed several years after cytokine treatment. Four patients had no prior therapy and were treated with the study drug immediately after diagnosis of metastases. At study entry three of these patients had a Karnofsky performance status (KPS) of 80%, two a KPS of 90%. Hemoglobin (Hgb) was below 10 g/dL in 5 patients. The median performance status of 90% (mean 91%) is identical to the group of patients who have not responded. The median Hgb of 9.8 g/dL (mean 10.97 g/dL) is also relatively low.

One patient achieved a complete objective remission. The objective response occurred late, more than six months after start of study therapy. Another patient experienced a relevant reduction of 59% in size of his target lesions. The response of both patients is ongoing at week 64 and 70, respectively, as evaluated in December 2001. The tumor regression occurred late, more than six months after start of study therapy. An explanation for the late response may be that the treatment duration with iv injections of the chimeric antibody was relatively short and a delayed immune response unrelated to ADCC developed.

The response is durable at more than one year and is still ongoing December 2001. The overall rate of clinical benefit (at least more than six months or objective response) is 25%. In addition it should be noted that at six months after start of study treatment, 87.5% (28/32) of the patients were still alive.

At the end of November 2001, an estimation of median survival was calculated to be at least 13.5 months.

At the end of January 2002, an estimation of median survival was calculated to be at least 15 months. This is significantly higher than the median survival of untreated patients (three months) and the median survival of patients treated with an FDA approved standard therapy, i.e. administration of high dose interleukin 2 (10-12 months).

Thus, it becomes evident that chimeric antibody G250 is a suitable therapeutic agent for the treatment of renal cell carcinoma. In a preferred embodiment the treatment comprises a surgical removal of the main tumor and a subsequent administration of G250, in order to eliminate metastases distributed throughout the body.

The invention claimed is:

1. A method for treating a renal cell carcinoma patient after tumor surgery, said method comprising:
   administering a monospecific and non-radiolabeled G250 monoclonal antibody to said patient after tumor surgery, wherein said G250 antibody increases the survival of said patient compared to untreated patients, and wherein said G250 antibody comprises:
   the heavy chain CDR sequences of SEQ ID NO:2; and
   the light chain CDR sequences of SEQ ID NO:4.

2. The method according to claim 1, wherein said G250 antibody is administered in an amount sufficient to treat metastases after tumor surgery.

3. The method according to claim 2, wherein said G250 antibody is administered once per week.

4. The method according to claim 1, wherein said G250 antibody is directly or indirectly obtained from hybridoma cell DSM ACC 2526.

5. The method according to claim 1, wherein said G250 antibody is a chimeric antibody, a humanized antibody, a single chain antibody, or a F(ab')2, a Fab', or a Fab antibody fragment.

6. The method according to claim 5, wherein the antibody is a chimeric G250 antibody.

7. The method according to claim 6, wherein said chimeric G250 antibody is coupled to a cytokine.

8. The method according to claim 7, wherein said cytokine is selected from the group consisting of IL-2, TNF and GM-CSF.

9. The method according to claim 4, wherein the G250 antibody is indirectly obtained from hybridoma cell DSM ACC 2526 by transfer of genetic material encoding antibody G250 or the antigen-binding site thereof into a receptor cell which then produces the antibody G250.

10. A method for treating a renal cell carcinoma patient after tumor surgery, said method comprising:
    administering a monospecific and non-radiolabeled G250 monoclonal antibody to said patient after tumor surgery, wherein said G250 antibody comprises the heavy and light chain CDR sequences of SEQ ID NOs: 2 and 4 respectively and wherein said method increases the survival of said patient compared to patients treated with high dose interleukin 2.

11. A method for treating a renal cell carcinoma patient after tumor surgery, said method comprising:
    administering a monospecific and non-radiolabeled G250 monoclonal antibody comprising the heavy and light chain CDR sequences of SEQ ID NOs: 2 and 4 respectively to said patient after tumor surgery, wherein said G250 antibody increases the survival of said patient to at least 6 months after start of treatment.

12. The method of claim 1, wherein the administering of said G250 antibody to the patient after tumor surgery generates an immune response against the renal cell carcinoma.

13. The method of claim 10, wherein said G250 antibody is directly or indirectly obtained from hybridoma cell DSM ACC 2526.

14. The method of claim 10, wherein said G250 antibody is a chimeric antibody, a humanized antibody, a single chain antibody, or a F(ab')2, a Fab', or a Fab antibody fragment.

15. The method of claim 10, wherein the administering of said G250 antibody to the patient after tumor surgery generates an immune response against the renal cell carcinoma.

16. The method of claim 11, wherein said G250 antibody is directly or indirectly obtained from hybridoma cell DSM ACC 2526.

17. The method of claim 11, wherein said G250 antibody is a chimeric antibody, a humanized antibody, a single chain antibody, or a F(ab')2, a Fab', or a Fab antibody fragment.

18. The method of claim 11, wherein the administering of said G250 antibody to the patient after tumor surgery generates an immune response against the renal cell carcinoma.

19. The method of claim 6, wherein the chimeric G250 antibody comprises a human Fc region.

20. The method of claim 14, wherein the G250 antibody is a chimeric antibody comprising a human Fc region.

21. The method of claim 17, wherein the G250 antibody is a chimeric antibody comprising a human Fc region.

22. The method of claim 1, wherein the renal cell carcinoma is metastatic renal cell carcinoma.

23. The method of claim 10, wherein the renal cell carcinoma is metastatic renal cell carcinoma.

24. The method of claim 11, wherein the renal cell carcinoma is metastatic renal cell carcinoma.

* * * * *